United States Patent [19]

Brossi

[11] Patent Number: 5,175,342
[45] Date of Patent: Dec. 29, 1992

[54] ESTERS OF 3-DEMETHYLTHIOCOLCHICINE AND N-ACYL ANALOGS

[75] Inventor: Arnold Brossi, Bethesda, Md.

[73] Assignee: The United States of America as represented by the Department of Health and Human Services, Washington, D.C.

[21] Appl. No.: 686,853

[22] Filed: Apr. 18, 1991

Related U.S. Application Data

[63] Continuation of Ser. No. 235,907, Aug. 24, 1988, abandoned.

[51] Int. Cl.$^5$ ............................................. C07C 69/00
[52] U.S. Cl. .................................... 560/139; 560/108; 558/271; 564/211; 564/212; 564/213
[58] Field of Search ............... 560/108, 139; 558/271; 564/211, 212; 574/213, 628; 514/529, 532, 546, 617

[56] References Cited

U.S. PATENT DOCUMENTS 2,820,029  1/1958  Muller et al.
3,997,506  12/1976  Dugat

OTHER PUBLICATIONS

De. Kalgon, K. et al., J. Carbohydr. Nucleosides, Nucleotides 2(2) 171–176 1975.
Capraso et al., pp. 48–57, "The Alkaloids" vol. XXIII 1984, Academic Press, N.Y.
Kerekes et al., J. Med. Chem. 28(9), 1204–1208, 1985.
Brossi et al., Medicinal Research Reviews 8(1), 77–94, 1988.
Kerekes et al., Helvetica Chimica Acta 68, 571–580, 1985.

*Primary Examiner*—Paul J. Killos
*Attorney, Agent, or Firm*—Robert Benson

[57] ABSTRACT

The present invention relates to esters of 3-demethylthiocolchicine and N-acyl analogs thereof having the following formula:

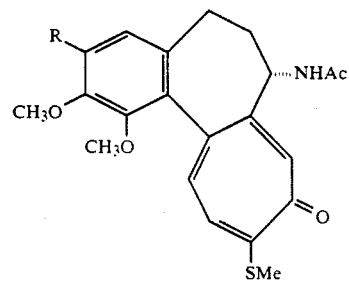

wherein R is O-CO-alkyl, O-CO-$CH_2$Oalkyl, O-CO-Phenyl, O-COOalkyl; the alkyl group having from 1 to 4 carbon atoms and the Ac group representing acetyl and its higher homologs, benzoyl, alkoxyacetyl, or haloacetyl.

The invention further relates to processes for preparing these ester compounds, pharmaceutical compositions thereof and methods for treating diseases such as gout, Mediterranean fever and liver disorders.

19 Claims, No Drawings

ESTERS OF 3-DEMETHYLTHIOCOLCHICINE AND N-ACYL ANALOGS

This is a continuation of application Ser. No. 07/235,907, filed Aug. 24, 1988, which is abandoned.

FIELD OF THE INVENTION

The present invention relates to esters of 3-demethylthiocolchicine and N-acyl analogs as substitutes of colchicine in diseases treated with colchicine, particularly liver disorders. Moreover, the invention is concerned with pharmaceutical compositions of the esters of 3-demethylthiocolchicine and N-acyl derivatives, methods of treating diseases such as gout, Mediterranean fever and liver disorders and a process for the preparation of the ester compounds.

BACKGROUND OF THE INVENTION 3-demethylthiocolchicine has broad-spectrum antitumor properties and has been reported to inhibit migration of amyloids (A. Brossi et al, Med. Res. Reviews. 1988, Vol. 8, pp. 77-94). Therefore, 3-demethylthiocolchicine is a substitute of colchicine having an improved therapeutic index. Although 3-demethylthiocolchicine is a known compound, the ester derivatives thereof having similar biological properties have not been reported.

U.S. Pat. No. 4,692,463 by Brossi, which is not prior art against the instant invention, describes the finding of potent antiinflammatory properties in 2,3-didemethylcolchicine and its derivatives. Although 3-demethylthiocolchicine is disclosed, the esters thereof are not reported. The contents of this patent are herein incorporated by reference.

U.S. Pat. No. 3,997,506 by Dugat discloses antimitotic and anti-gout derivatives of thiocolchicine.

U.S. Pat. No. 3,816,396 discloses a process for the preparation of glucoside derivatives of thiocolchicine.

U.S. Pat. No. 2,820,029 by Muller et al discloses thio-derivatives of colchiceine compounds and a process of making the same.

A publication by Kerekes et al entitled "Esters of 1-0-Demethylthiocolchicines: Formation of Isomers in Chloroform Solution", Helvetica Chimica Acta. Vol. 68, 1985, p. 579, discloses 3-0-Acetyl-10-demethoxy-3-0-demethyl-10(methylthio) colchicine.

A French language publication by Velluz et al entitled "La thiocolchicine. III. - Etude de quelques S-alcoyl-thiocolchiceines", Memoires presentes a la Societe Chimique, pp. 194-197, discloses the preparation and study of thiocolchicine.

SUMMARY OF THE INVENTION

This invention relates to novel esters of 3-demethylthiocolchine and N-acyl analogs thereof. The invention further relates to pharmaceutical compositions of these 3-demethylthiocolchine and N-acyl analogs as well as to methods of treating diseases treated with colchicine, particularly liver disorders. Moreover, the invention is also directed to a process for preparing novel esters of 3-demethylthiocolchine and N-acyl analogs.

DETAILED DESCRIPTION OF THE INVENTION

The compounds of the invention will hereinafter be described in greater detail.

Description of Esters of 3-demethylthiocolchicine and N-acyl analogs thereof

More particularly, the present invention relates to esters of 3-demethylthiocolchicine and N-acyl analogs thereof having the formula:

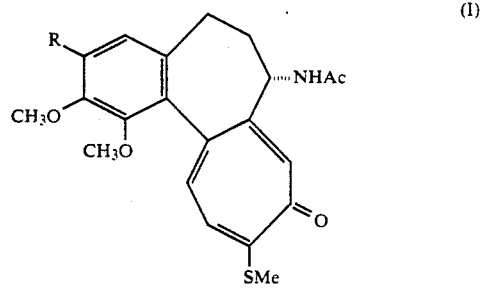

(I)

wherein R is selected from the group consisting of O-CO-alkyl, O-CO-CH$_2$Oalkyl, O-CO-phenyl, O-COOalkyl; the alkyl group having 1 to 4 carbon atoms, the Ac group being acetyl and its higher homologs, benzoyl, haloacetyl, or alkoxyacetyl.

Representative examples of alkyl groups having 1 to 4 carbon atoms include methyl, ethyl, n-propyl, isopropyl, n-butyl, isobutyl, tert-butyl and sec-butyl.

Higher homologs of the acetyl group include those acetyl groups containing 1 to 8 carbon atoms including saturated fatty acids, and more particularly those acetyl groups containing 1 to 4 carbon atoms.

Representative examples of the alkoxyacetyl group include those alkoxy groups containing 1 to 8 carbon atoms, particularly 1 to 4 carbon atoms.

Suitable examples of the haloacetyl group include mono-substituted and tri-substituted haloacetyl groups including fluoroacetyl, chloracetyl, bromoacetyl, and trifluoroacetyl wherein the acetyl group is as defined above. Preferably, the mono and trifluoroacetyl groups are used.

The preferred compounds of the invention are selected from the group consisting of 3-acetyl-3-demethylthiocolchicine, 3-ethoxyacetyl-3-demethylthiocolchicine, 3-ethoxycarbonyl-3-demethylthiocolchicine, 3-benzoyl-3-demethylthiocolchicine, N-butyryl-deacetyl-3-demethylthiocolchine, and 3-butyryl-3-demethylthiocolchicine.

Additional preferred compounds of the invention are selected from the group consisting of 3-butoxycarbonyl-3-demethylthiocolchicine, N-butyryl-3-demethyldeacetylthiocolchine butyrate, N-trifluoroacetyl-3-demethyldeacetylthiocolchicine, N-fluoroacetyl-3-demethyl-deacetylthiocolchicine.

3-demethylcolchicine is a natural product (H. G. Capraro and A. Brossi, The Alkaloids. Vol. 23, Academic Press, 1984, p.10) which occurs, in addition to colchicine, in a variety of plant species such as Colchicum autumnale and Gloriosa superba. 3-demethylcolchicine may be converted by reaction with sodium methylthiolate into 3-demethylthiocolchicine which on further reaction at the OH position on the phenol reacts with acylating agents such as butyric anhydride or esterification agents such as ethyl chloroformate to produce the ester derivatives shown in formula (I), wherein R is defined above.

3-demethylthiocolchicine prepared from the commercial drug thiocolchicoside (e.g. obtained from Roussel-Uclaf) by treatment with 80% phosphoric acid (P. N. Sharma and A. Brossi, *Heterocycles,* 1983, Vol. 20, p.1587) has potent antitumor activity in experimental animals (P. Kerekes, P. N. Sharma, A. Brossi, C. F. Chignell and F. R. Quinn, *J. Med. Chem.,* 1985, Vol. 28, p.1204) and inhibits amyloid migration (M. Ravid, M. Gotfried and A. Brossi, "Amyloidosis" 1988, Plenum Press, New York, in press). These activities in this series of compounds parallel their affinity for tubulin and, therefore, a tublin-affinity test allows an assessment of the potential medical uses of these compounds (A. Brossi, H. J. C. Yeh, M. Chrzanowska, J. Wolff, E. Hamel, C. M. Lin, F. Quinn, M. Suffness and J. V. Silverton, *Med. Res. Reviews,* 1988, Vol. 8, pps.77-94)

Using such data, which are shown in Example 9, it is clear that the ester derivatives covered by formula (I) have similar biological effects as the parent phenol and are at least as potent as colchicine. 3-demethylthiocolchicine has emerged from elaborate study as a less toxic analog of colchicine with a larger therapeutic index (M. Ravid, M. Gotfried and A. Brossi, "Amyloidosis", 1988, Plenum Press, New York, in press) and its ester derivatives can, therefore, be considered to represent useful compounds for the treatment of gout, Mediterranean fever (FMF) and liver disorders such as cirrhosis of the liver, tumors and inflammation of unspecific origin.

The ester derivatives covered by formula (I) above are prepared from natural (-)-3-demethylcolchicine (H. G. Capraro and A. Brossi, "The Alkaloids", Vol. 23, Academic Press, 1984, p.10.) via (-)-3-demethylthiocolchicine obtained from the former by reaction with sodium methylthiolate in water. 3-demethylcolchicine also can be obtained from colchicoside as a natural alkaloid (H. G. Capraro and A. Brossi, "The Alkaloids", Vol. 23, Academic Press, 1984, p.10) which can be converted into 3-demethylcolchicine by treatment with 80% phosphoric acid (M. Rosner, H. G. Capraro, A. E. Jacobson, L. Atwell, A. Brossi, M. A. Torio, T. H. Williams, R. H. Sik and C. F. Chignell, *J. Med. Chem.* 1981, Vol. 24, p.257.)

Methods for preparing esters of 3-demethylthiocolchicine and N-acyl derivatives thereof will hereinafter be described in greater detail.

Methods for preparing esters of 3-demethylthiocolchicine and N-acyl derivatives thereof Accordingly, the invention is further directed to a process for the preparation of 3-demethylthiocolchicine or the esters thereof from 3-demethylcolchicine obtained from colchicoside. 3-demethylthiocolchicine can be obtained from 3-demethylcolchicine by treatment with an alkaline salt of methyl mercaptane commercially available as sodium or potassium methylthiolate and the reaction occurs in water at temperatures between about 0° and 30° C., preferably at room temperature. Material prepared by this route is converted into the ester analogs as shown in the following reaction scheme.

FORMULA SCHEME

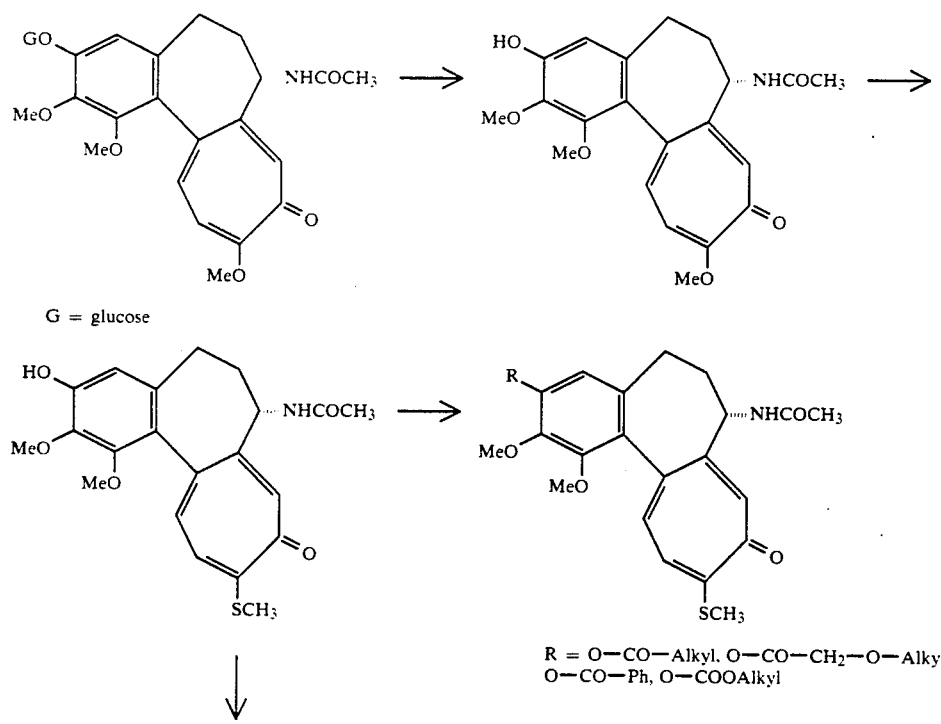

-continued
FORMULA SCHEME

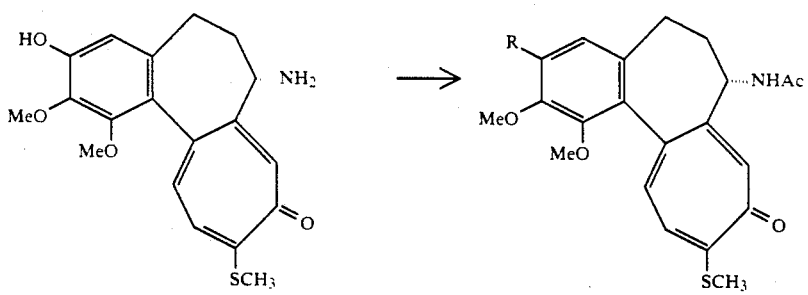

R as above and Ac = acyl, benzoyl and alkoxyacetyl, trifluoroacetyl, haloacetyl.

The esterification may proceed via conventional techniques, such as treating the phenol with acid chloride in the presence of sodium hydroxide (Schotten-Baumann reaction), or with acylanhydride in the presence of pyridine or triethylamine, or with alkylchloroformate in the presence of pyridine.

The ester analogs are neutral materials, which can be crystallized from solvents such as acetone, ethylacetate, isopropyl ether, chloroform-pentane, etc. They also can be chromatographed on aluminum oxide or silica gel and eluted with mixtures of solvents such as methylenechloride/methanol 95:5 or 90:10 etc. The compounds are optically active and have the same configuration as colchicine.

The acetyl group in 3-demethylthiocolchicine can be replaced by other acyl groups such as propionyl, butyryl, benzoyl, trifluoroacetyl, through acid hydrolysis of 3-demethylthiocolchicine with 20% sulfuric or hydrochloric acid (e.g. for about 3 hours) and treatment of the 3-demethyldeacetylthiocolchicine with anhydrides such as butyric anhydride, propionic anhydride, benzoic anhydride etc. produces the corresponding N-acyldeacetylthiocolchicine 3-butyrate, N-benzoyldeacetylthiocolchicine 3-benzoate etc. These esteramides on hydrolysis with potassium carbonate in aqueous methanol afford the corresponding acyldeacetylthiocolchicine analogs which can be esterified as mentioned above. For example, N-butryryldeacetyl-3-demethylthiolcolchicine prepared by this sequence of reactions affords after treatment with acetic anhydride in pyridine the corresponding acetate. Procedures involving acid hydrolysis of colchicine with sulfuric acid and treatment with anhydrides are set forth in Dumont et al, *Journal of Organic Chemistry*, June 27, 1986, pp 2515-2521, by the American Chemical Society, which is herein incorporated by reference.

The following Examples are intended to illustrate processes for preparing the claimed invention and will enable others skilled in the art to understand the invention more completely. However, the invention should not be interpreted as being limited to only these representative examples.

EXAMPLE 1

A mixture of 250 mg of colchicoside and 2 ml of 85-86% $H_3PO_4$ is stirred at 25° C. for 24 hours. The yellow solution is diluted with 10 ml of water, adjusted to pH 5 by addition of 2N NaOH and extracted with methylene chloride. The extracts are dried ($Na_2SO_4$), evaporated and chromatographed on $Al_2O_3$ (basic, Alfa Division, $CH_2Cl_2$/MeOH=95:5). The appropriate fractions after evaporation of solvent and crystallization from acetone afford 180 mg (89%) of 3-demethylcolchicine: mp 176°-177° C. (resolidification at 205°-210° C. and 2nd mp 270° C. (dec.), $[\alpha]_D = -151°$ (solvate crystal, $CHCl_3$).

3-demethylcolchicine (600 mg) in water (6 ml) was added with sodium methanethiolate (Fluka, 806 mg). The reaction was stirred for 24 hours, diluted with 2% acetic acid (15 ml) and then extracted with chloroform (3×100 ml) to give a yellow powder (530 mg). Crystallization from acetone gave 3-demethylthiocolchicine. mp 310° C., $[\alpha]_D = -259°$ (c=0.2, $CHCl_3$).

EXAMPLE 2

3-ethoxyacetyl-3-demethylthiocolohioine is prepared from 3-demethylthiocolchicine by reaction with ethoxyacetic anhydride in pyridine at room temperature. Crystallization in acetone yields the desired final product. mp 247° C., $[\alpha]_D = -116°$ (c=0.1, $CHCl_3$).

EXAMPLE 3

3-demethylthiocolchicine (100 mg) is dissolved in methylene chloride (3 ml) and triethylamine (0.5 ml) is added with ethylchloroformate (0.5 ml) and the reaction mixture is left under stirring at room temperature for 3 hours. The reaction mixture is then diluted with methylene chloride (20 ml), washed with 2N HCl, saturated sodium carbonate solution and brine, to afford after evaporation of solvent and crystallization from ethylacetate the ethylcarbonate of 3-demethylthiocolchicine. mp 249° C., $[\alpha]_D = -128°$ (c=0.1, $CHCl_3$).

EXAMPLE 4

3-demethylthiocolchicine (100 mg) is stirred in 20% sulfuric acid at 90° C. for 6 hours. The reaction mixture is adjusted to pH 7 with sodium carbonate solution and extracted with chloroform-isopropanol in a ratio of 3:1 thereof, the organic layer washed with brine, and dried over $Na_2SO_4$ and concentrated to afford 98 mg of a crude product which after crystallization from methylene chloride produces 66 mg of N-deacetyl 3-demethylthiocolchicine. mp 182°-183° C.; $[\alpha]_D = -192°$ (c=0.125, $CHCl_3$).

To a solution of the deacetyl compound above (66 mg) in pyridine (1 ml) is added butyric anhydride (0.11 ml) and the reaction mixture is stirred for 2 hours at room temperature. Solvent is evaporated in vacuo, the residue dissolved in methylene chloride, the organic layer washed with brine, dried over $Na_2SO_4$ and concentrated to produce 80 mg of the 3-demethyl-N- butyryldeacetylthiocolchicine butyrate as yellow crystals. mp 192° C., $[\alpha]_D = -146°$ (c=0.46, CHCl$_3$).

For conversion into 3-demethyl-N-butyryldeacetylthiocolchicine the above ester (55 mg) is dissolved in acetone (2 ml) and stirred with a solution of potassium carbonate (60 mg) in water (1 ml) at 60° C. for 24 hours. The reaction mixture is poured into chloroform, the organic layer washed with water, brine, dried over Na$_2$SO$_4$, concentrated to dryness and the residue crystallized from methylene chloride-ether to produce 20 mg of the yellow phenol. mp 153°-155° C.; $[\alpha]_D = -302°$ (c=0.13, CHCl$_3$).

EXAMPLE 5

3-demethylthiocolchicine (100 mg) in pyridine (1 ml) is stirred at room temperature for 2.5 hours with butyric anhydride (0.2 ml). The solvent is evaporated and the residue is dissolved in chloroform. The chloroform solution is washed with 5% HCl, water and sodium carbonate solution and dried over MgSO$_4$. Crystallization from ethyl acetate produces yellow crystals of 3-butyryl-3-demethylthiocolchicine. mp 232° C.; $[\alpha]_D = -138.8°$ (c=0.11, CHCl$_3$).

EXAMPLE 6

3-demethylthiocolchicine (100 mg) in pyridine (3 ml) is added with butylchloroformate (0.2 ml) under ice cooling. After 1 hour standing, the reaction mixture is adjusted to pH 5 by addition of 2N HCl and extracted with chloroform. After washing and drying as described in Example 5, 108 mg of 3-butoxycarbonyl-3demethylthiocolchicine is obtained as a yellow powder. mp 212°-215° C.; $[\alpha]_D = -110.8°$ (c=0.3, CHCl$_3$).

EXAMPLE 7

3-demethylthiocolchicine (50 mg), ether (20 ml), anhydrous sodium carbonate (147 mg) and trifluoroacetic anhydride (0.2 ml) are mixed at 0° C. and left standing for 2 hours. After washing and drying as described in Example 5, a crude extract is obtained after being chromatographed through a silica gel column with a chloroform-methanol mixture 98:2 to produce N-trifluoroacetyl-3-demethylthiocolchicine as a yellow crystals. mp 175°-177° C., MS 455 (M$^+$), single spot on TLC, $[\alpha]_D = -176°$ (c=0.35, CHCl$_3$).

The compositions of the invention will hereinafter be described in greater detail.

Compositions containing esters of 3-li demethylthiocolchicine and N-acyl derivatives thereof The compounds of the present invention can be made into pharmaceutical compositions by combination with appropriate medical carriers or diluents. For example, the compounds can be mixed with starch, sugars and other inert ingredients commonly used to make tablets and used as tablets for oral application. The compounds can also be dissolved in oils, propyleneglycol or other solvents commonly used to prepare injectable solutions. Such preparations can be used for the treatment of gout, FMF, liver disorders, such as liver cirrhosis and as antitumor and antiinflammatory agents. For topical application, they can be formulated as ointments or creams.

More specifically, the compounds of the present invention may be formulated into preparations in solid, semisolid, liquid or gaseous form such as tablets, capsules, powders, granules, ointments, solutions, suppositories, and injections, in usual ways for oral or parenteral administration.

The following methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds in the case of oral preparation may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the present invention may be formulated into preparations for injections by dissolving, suspending or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds of the invention may be combined with other compounds such as with other antitumor agents.

The following example further illustrates the composition of the present invention and will enable others skilled in the art to understand the invention more completely. It is understood that the invention is not limited to the Example below.

EXAMPLE 8

2 mg of 3-butyryl-3-demethylthiocolchicine as the active ingredient is combined with 187 grams of microcrystalline cellulose as a carrier, 9 mg of stearic acid and 2 mg of colloidal silica. These materials are pressed to form a tablet.

Methods of treating various diseases or disorders with the compound or composition of the invention will hereinafter be described in greater detail.

Methods for treating diseases or disorders

The desirable dose of the compounds of the present invention varies with the subject, drug form, method and period of administration. However, in order to obtain desirable effects, generally it is recommended to administer 0.1 mg to 40 mg/kg, preferably 0.5 to 10 mg/kg, body weight of the compounds of the present invention. In terms of composition, compounds should be present between 0.1 to 100% by weight.

Biological Data

The following examples further illustrate that the ester compounds of present invention have potential as antimicrotubule agents in mammals such as humans and will enable others skilled in the art to understand the invention more completely. Of course, it is understood that the invention is not limited to the Examples below.

EXAMPLE 9

Compounds were evaluated both as inhibitors of tubulin polymerization and as inhibitors of the binding of radiolabeled colchicine to tubulin. The claimed compounds were compared to colchicine, 3-demethylcolchicine, thiocolchicine, and 3-demethylcolchicine. Additional procedures for evaluating these compounds are set forth by H. G. Capraro and A. Brossi, "The Alkaloids", Vol. 23, Academic Press, 1984, pp. 48–57, which is herein incorporated by reference. Moreover, this publication further shows that a good correlation exists between compounds active in vivo and their tubulin affinity in vitro.

| Compound | Inhibition of tubulin polymerization IC$_{50}$ (M) | Inhibition of [$^3$H]colchicine binding % inhibition |
| --- | --- | --- |
| colchicine | 2–3 | 27 |
| 3-demethylcolchicine | 2–3 | 23 |
| thiocolchicine | 1–2 | 54 |
| 3-demethylthiocolchicine | 1–2 | 36 |
| 3-acetyl-3-demethyl-thiocolchicine | 2–3 | 25 |
| 3-butyryl-3-demethyl-thiocolchicine | 1–2 | 54 |
| 3-benzoyl-3-demethyl-thiocolchicine | 4–5 | 19 |
| 3-ethoxycarbonyl-3-demethyl-thiocolchicine | 1–2 | 49 |
| 3-ethoxylacetyl-3-demethyl-thiocolchicine | 1–2 | 42 |

The polymerization assay includes a drug-tubulin preincubation prior to GTP addition to allow slow binding drugs like colchicine to interact with the protein. The value in the table indicates the range of drug concentration required to obtain 50% inhibition of the extent of the polymerization reaction. Any value below 10 μM indicates a potent antimicrotubule agent with significant antimitotic potential.

The colchicine binding assay was performed without a drug-tubulin preincubation. The potential inhibitors (including nonradiolabeled colchicine) were present at a molar ratio with the radiolabeled colchicine. (A concentration of radiolabeled colchicine which is rate-limiting is used. As a consequence, equimolar nonradiolabeled colchicine inhibits less than 50%.) The values in the table thus reflect both the affinity of the agents for tubulin relative to that of colchicine and relative binding rates of the agents relative to that of colchicine. Any inhibitory activity at all at the low drug concentrations used in this experiment (5 μM) indicates significant binding at the colchicine site.

The invention is also directed to a method of treating gout, Mediterranean fever and liver disorders which comprises administering to a patient a pharmaceutically effective amount of the instant composition. Administration is preferably by injection, orally, or with cream or ointment.

EXAMPLE 10

A tablet is first formulated and prepared as in Example 8. The tablet is orally administered to a patient and represents a typical daily dosage.

The invention being thus described, it will be obvious that the same way be varied in many ways. Such variations are not to be regarded as a departure from the spirit and scope of the present invention, and all such modifications as would be obvious to one skilled in the art are intended to be included within the scope of the following claims.

What is claimed is:

1. A compound of the formula

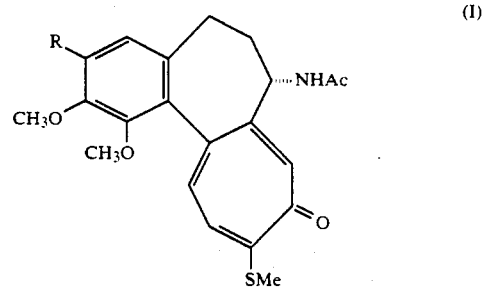

(I)

wherein R is selected from the group consisting of O-CO-alkyl, O-CO-CH2-O-alkyl, O-CO-phenyl, and O-COOalkyl, the alkyl group having 1 to 4 carbon atoms, the Ac group being acetyl and its higher homologs, haloacetyl or alkoxyacetyl; or R is hydroxy and Ac is chosen from the group consisting of trifluoroacetyl and fluoroacetyl with the proviso that when R is O-CO-alkyl, Ac can only be acetyl, haloacetyl or alkoxyacetyl, and the alkyl in O-CO-alkyl cannot be methyl.

2. The compound of claim 1, wherein the compound is selected from the group consisting of 3-ethoxyacetyl-3-demethylthiocolchicine, 3-ethoxycarbonyl-3-demethylthiocolchicine, 3-benzoyl-3-demethylthiocolchicine, and 3-butyryl-3-demethylthiocolchicine.

3. The compound of claim 1, wherein the compound is selected from the group consisting of 3-butoxycarbonyl-3-demethylthiocolchicine, N-trifluoroacetyl-3-demethyldeacetylthiocolchicine, N-fluoroacetyl-3-demethyldeacetylthiocolchicine.

4. The compound of claim 2, wherein the compound is 3-ethoxyacetyl-3-demethylthiocolchicine.

5. The compound of claim 2, wherein the compound is 3-ethoxycarbonyl-3-demethylthiocolchicine.

6. The compound of claim 2, wherein the compound is 3-benzoyl-3-demethylthiocolchicine.

7. The compound of claim 2, wherein the compound is 3-butyryl-3-demethylthiocolchicine.

8. A pharmaceutical composition, which comprises a pharmaceutically effective amount of the compound of claim 1 and a pharmaceutically acceptable carrier therefor.

9. A pharmaceutical composition, which comprises a pharmaceutically effective amount of the compound of claim 2 and a pharmaceutically acceptable carrier therefor.

10. A method for treating gout, Mediterranean fever and liver disorders which comprises administering to a patient a therapeutically effective amount of the composition of claim 8.

11. The method of claim 10, wherein the liver disorders which are treated are cirrhosis of the liver, tumor growth or inflammation.

12. A method for treating gout, Mediterranean fever and liver disorders which comprises administering to a patient a therapeutically effective amount of the composition of claim 9.

13. The method of claim 12, wherein the liver disorders which are treated are cirrhosis of the liver, tumor growth or inflammation.

14. The method of claim 12, which comprises administering to a patient 0.5 to 10 mg/kg body weight of the compound.

15. The method of claim 13, which comprises administering to a patient 0.5 to 10 mg/kg body weight of the compound.

16. The method of claim 12, wherein the patient is treated by injection, orally, or with cream or ointment.

17. A method of inhibiting the formation of microtubules in mammals which comprises administering to a mammal a therapeutically effective amount of a compound of the formula

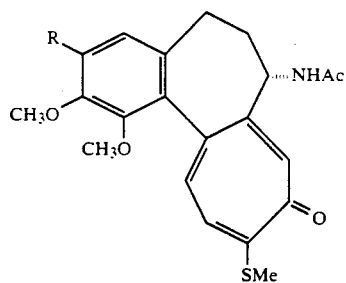

wherein R is chosen from the group consisting of O-CO-alkyl, O-CO-CH$_2$-O-alkyl, O-CO-phenyl, and O-COO-alkyl, the alkyl group having 1 to 4 carbon atoms, the Ac group being acetyl and its higher homologs, benzoyl, haloacetyl or alkoxyacetyl; or R is hydroxy and Ac is chosen from the group consisting of butyryl, trifluoroacetyl or fluoroacetyl, with the proviso that if R is O-CO-CH$_3$, then Ac cannot be acetyl.

18. The method of claim 17, wherein the mammal is suffering from gout, mediterranean fever or liver disorder.

19. The method of claim 18, wherein said liver disorder is cirrhosis of the liver, tumor or inflammation.

* * * * *